US006231531B1

(12) United States Patent
Lum et al.

(10) Patent No.: US 6,231,531 B1
(45) Date of Patent: May 15, 2001

(54) APPARATUS AND METHOD FOR MINIMIZING PAIN PERCEPTION

(75) Inventors: Paul Lum; Michael Greenstein, both of Los Altos; Edward Dennis Verdonk, San Jose; Tad Decatur Simons, Palo Alto; Dominique Freeman, Pescadero; Ganapati Ramnath Mauze, Sunnyvale; David King, Palo Alto; Jerry Zawadzki, San Jose, all of CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/289,884

(22) Filed: Apr. 9, 1999

(51) Int. Cl.⁷ ...................................................... A61H 1/00
(52) U.S. Cl. ............................ 601/46; 606/181; 606/182; 600/573; 600/583
(58) Field of Search .......................... 601/46, 2; 604/131, 604/148, 154, 22; 600/583, 577, 578; 606/181, 182, 183, 185

(56) References Cited

U.S. PATENT DOCUMENTS

| | | |
|---|---|---|
| 2,258,857 | 10/1941 | McCann . |
| 3,620,209 | 11/1971 | Kravitz . |
| 4,462,405 | 7/1984 | Ehrlich . |
| 4,637,403 * | 1/1987 | Garcia et al. .......................... 600/573 |
| 5,035,704 | 7/1991 | Lambert et al. . |
| 5,647,851 | 7/1997 | Pokras . |
| 5,662,127 * | 9/1997 | De Vaughn ............................ 606/181 |
| 5,857,983 * | 1/1999 | Douglas et al. ....................... 600/538 |
| 5,947,957 * | 9/1999 | Morris .................................... 606/13 |
| 5,951,493 * | 9/1999 | Douglas et al. ....................... 600/583 |
| 5,997,561 * | 12/1999 | Bocker et al. ......................... 606/182 |

FOREIGN PATENT DOCUMENTS

WO 97/28741  8/1997  (WO) .

OTHER PUBLICATIONS

Bruck et al., "Procedures for the Collection of Diagnostic Blood Specimens by Skin Puncture", Third Edition, pp. 1–16, *NCCLS* Jul. 1991, vol. 11, No. 11.
Ludel, *Introduction to Sensory Processes*, pp. 279–307, 1978.
Guyton, "Sensory Receptors; Neuronal Circuits for Processing Information", pp. 495–506, *Text of Medical Physiology*, 1991.
Terzis et al., *The Peripheral Nerve: Structure, Function and Reconstruction*, pp. 1–37, 1990.
Melzack et al., "Pain Mechanisms: A New Theory", pp. 971–979, *Science Magazine*, Nov. 19, 1965, vol. 150.
Wall, "The Gate Control Theory of Pain Mechanisms: A Re–examination and Re–statement", pp. 1–18, *Brain*, 1978.
Zoppi et al., "Pain Threshold Changes By Skin Vibratory Stimulation in Healthy Subjects", pp. 439–443, 1991.

(List continued on next page.)

*Primary Examiner*—Justine R. Yu (57) ABSTRACT

An apparatus and method for minimizing a subject's pain perception during an invasive medical procedure, such as blood sampling and the like. The apparatus can include a receiving surface constructed to contact a portion of the subject's skin and a vibratory mechanism associated with the receiving surface such that the vibratory mechanism transmits vibrations through the receiving surface and to the subject's skin. An invasive sharp can be substantially permanently supported and moveably disposed with respect to the receiving surface such that the invasive sharp reciprocates between a first position in which the sharp is spaced from the receiving surface, away from the subject's skin, and a second position in which at least a portion of the sharp protrudes through an opening in the receiving surface.

20 Claims, 5 Drawing Sheets

OTHER PUBLICATIONS

Yarnitsky et al., "Vibration Reduces Thermal Pain in Adjacent Dermatomes", pp. 75–77, *Pain*, 1997, vol. 69.

Melzack et al., "Masking and Metacontrast Phenomena in the Skin Sensory System", pp. 35–46, *Experimental Neurology*, vol. 8, 1963.

Lindblom et al., "The Discharge from Vibration–Sensitive Receptors in the Monkey Foot", pp. 401–417, *Experimental Neurology*, vol. 15, 1966.

Talbot et al., "The Sense of Flutter–Vibration, Comparison of the Human Capacity With Response Patterns of Mechanoreceptive Afferents From the Monkey Hand", pp. 301–334, Dept. of Physiology, The Johns Hopkins University School of Medicine, 1968.

\* cited by examiner

APPARATUS AND METHOD FOR MINIMIZING PAIN PERCEPTION

BACKGROUND OF THE INVENTION

1. Field of the Invention

The present invention is directed to an apparatus and method for minimizing a subject's pain perception during a medical procedure and, more specifically, to a modular system for obtaining a blood sample from a subject while minimizing pain perception.

2. Description of the Related Art

Due to the pain often associated with invasive medical procedures, such as blood sampling and the like, many people are reluctant to visit a doctor or to obtain needed diagnostic tests and other beneficial medical procedures. This is particularly true in the case of children, who, if traumatized, may develop a lasting fear of doctors and/or medical procedures that can persist into adolescence or even adulthood. This reluctance is often aggravated in situations where multiple punctures must be made to obtain the necessary quantity of blood or other bodily fluid. In this regard, data published by H. Fruhstorfer, et al. in *Practical Diabetes International*, Vol. 12, No. 4, July/August 1995, demonstrated that increasing penetration depth provides more blood from a single puncture. Unfortunately, however, increased penetration depth often increases pain perception during the procedure.

Previous attempts to reduce pain perception during invasive procedures include various devices and methods for introducing a local anesthetic, such as Lidocaine® or ethylchloride, prior to piercing. For example, transdermal electrode patches have been used to drive a local anesthetic by ionic transport into the dermal tissue layer before intravenous line placement. Transcutaneous electrical nerve stimulation (TENS) has also been used to relieve both acute and chronic pain. TENS involves the application of a constant current to the skin for durations ranging from a few minutes to as long as 30 minutes.

Another method and apparatus for reducing pain perception was disclosed by McCann in U.S. Pat. No. 2,258,857. The apparatus includes a vibrating unit having a contacting element adapted to contact a patient's face during a dental procedure. In operation, the patient activates the vibrating unit and holds the unit in place on his face, proximate the ear. The vibrations purportedly distract and confuse the patient's nerve functions, thereby lessening pain perception by preventing the patient's nerve sense from locating the exact point of the pain. Also, the noise produced by the unit purportedly overcomes all noises produced by other instruments during the dental procedure, thereby further distracting the patient from the dental procedure.

A device for reducing pain perception during injections was disclosed by Kravitz in U.S. Pat. No. 3,620,209. The device includes a casing adapted to be pressed against a patient's skin, a strap for securing the casing to the patient, and vibratory means positioned within the casing. In operation, the casing is secured to the patient, and the vibratory means is actuated. After the patient's skin is vibrated sufficiently to stimulate the pain center of the skin, a needle (which does not form part of the device) is injected into the patient, proximate the device, and the pain of the injection is purportedly minimized by the vibration.

Another device for reducing pain perception associated with injections was disclosed by Pokras in U.S. Pat. No. 5,647,851. The device is a portable, hand held vibrating injection device including an injection needle and a housing enclosing a vibrator. In operation, the vibrator vibrates the needle as it penetrates the patient's skin, thereby purportedly lessening the amount of pain and discomfort experienced by the patient. The vibration of the needle also purportedly accelerates migration of the injected medication into the subcutaneous tissue and away from the puncture site.

Various other approaches and apparatus have been proposed to reduce the perception of pain while drawing blood samples, such as those disclosed in U.S. Pat. No. 4,462,405, U.S. Pat. No. 5,035,704 and WO 97/28741.

SUMMARY OF THE INVENTION

The present invention is directed to an apparatus and method for minimizing a subject's pain perception during an invasive medical procedure, such as blood sampling and the like. The unique configuration of the apparatus of the present invention allows invasive procedures to be performed on a subject with minimal discomfort.

The apparatus includes a receiving surface constructed to contact a portion of the subject's skin and a vibratory mechanism associated with the receiving surface such that the vibratory mechanism transmits vibrations through the receiving surface and to the subject's skin. An invasive sharp is substantially permanently supported and moveably disposed with respect to the receiving surface such that the invasive sharp can reciprocate between a first position in which the sharp is spaced from the receiving surface, away from the subject's skin, and a second position in which at least a portion of the sharp protrudes through an opening in the receiving surface.

In various alternative embodiments, it is contemplated that the apparatus may further include a roller unit moveably disposed relative to the invasive sharp such that the roller unit applies a force on the sharp that moves the sharp from the first position to the second position. The roller unit may contain a roughened roller so that movement of the roller transmits vibrations through the receiving surface. The apparatus may also include a resilient member associated with the invasive sharp such that the resilient member moves the sharp from the second position to the first position when the force applied by the roller unit is removed. If desired, a spring or an elastomeric sheet may serve as the resilient member.

Another aspect of the invention includes a modular system for obtaining a blood sample from a subject with minimal pain perception. The system includes a housing and a removable module disposed within the housing. The module has a receiving surface constructed to contact a portion of the subject's skin. An invasive sharp is moveably disposed within the removable module such that the sharp reciprocates between a first position in which the sharp lies below the receiving surface and a second position in which at least a portion of the invasive sharp protrudes through an opening in the receiving surface. A vibratory mechanism associated with the receiving surface transmits vibrations through the receiving surface and to the subject's skin.

In alternative embodiments, the system may include a channel adapted to receive a body fluid from the subject and to direct the body fluid to a point of use. The channel may include a capillary tube. The system may further include a roller unit moveably disposed within the housing such that the roller unit applies a force on the sharp that moves the sharp from the first position to the second position. The roller unit may contain a roughened roller so that movement of the roller transmits vibrations through the receiving surface. The apparatus may also include a resilient member associated with the invasive sharp such that the resilient member moves the sharp from the second position to the first position when the force applied by the roller unit is removed.

In another aspect of the present invention, a method is provided for minimizing a subject's pain perception during a medical procedure. The method includes supporting an invasive sharp with respect to a receiving surface having an opening therethrough. The receiving surface is vibrated while a portion of the surface is in contact with the subject's skin. The subject's skin is pierced with the sharp while the skin is contacting the receiving surface. The sharp is then withdrawn from the skin.

In various alternative embodiments, the piercing may be accomplished by actuating a roller unit moveably disposed relative to the invasive sharp such that the roller unit applies a force on the sharp that moves it from a first position to a second position in which the sharp pierces the subject's skin. The method may further comprise the step of withdrawing the invasive sharp from the subject's skin with a resilient member associated with the sharp such that the resilient member moves the sharp from the second position to the first position when the force applied by the roller unit is removed.

BRIEF DESCRIPTION OF THE DRAWINGS

Other objects and features of the present invention will become apparent from the detailed description when read in light of the attached drawings. It is to be understood that these drawings are for illustration purposes only and are not intended to define the limits of the present invention, wherein.

DETAILED DESCRIPTION OF PREFERRED EMBODIMENTS

The present invention is directed to an apparatus and method for minimizing a subject's pain perception during a medical procedure. The unique configuration of the apparatus of the present invention allows invasive procedures to be performed on a subject with minimal discomfort. The present invention exploits a concept known as the Gate Control Theory, which suggests that the degree of pain perceived by a subject as resulting from an invasive procedure can be lessened by applying an additional, non-invasive stimulation proximate the puncture site, which will block out the pain sensory neural pathways.

Pain can generally be classified into one of two categories, "fast pain" and "slow pain." "Fast pain" typically occurs within 0.1 second after the pain stimulus is applied. "Slow pain" typically begins a second or even minutes after the stimulus has occurred. Pain receptors in the skin are free nerve endings and are classified as mechanical, thermal, or chemical. Fast pain is generally associated with mechanical and thermal types of receptors; whereas, slow pain can be detected by all three types.

Free pain receptors utilize two separate pathways for transmitting pain signals into the central nervous system, the "fast, sharp pathway" and the "slow, chronic pathway." Fast pain signals are transmitted from the peripheral nerves to the spinal cord by small, type A fibers at velocities of about 6 m/sec to about 30 m/sec, while slow pain signals are transmitted by type C fibers at a rate of about 0.5 m/sec to about 2 m/sec. The two pathways enter the spine through the Tract of Lissauer that lies posterior to the dorsal horn of the cord gray matter. The fast, type A pain fibers transmit mechanical and thermal pain. Type A fibers terminate in the lamina marginalis of the dorsal horn and where they excite second order neurons of the neospinalthalamic tract. Certain fibers from the neospinalthalamic tract terminate at the reticular areas of the brain stem, but most pass all the way to the thalamus, terminating in the ventrobasal complex along with the dorsal column-medial lemniscal tract. From these areas, the pain signals are transmitted to the somatic sensory cortex and other areas in the brain.

When the type A fibers are blocked without blocking the type C fibers by moderate compression of the nerve trunk, fast, sharp pain disappears. When the type C fibers are blocked and the type A fibers are not blocked, by local anesthetic or the like, slow, chronic pain disappears. When a pain stimulus is applied, double pathways are responsible for the immediate, sharp pain sensation followed by the slow, dull pain sensation. The sharp, fast pain sensation typically induces a person to react and remove the pain stimulus, while the dull pain temporarily remains. Accordingly, type A pain can be localized more quickly and exactly in the different parts of the body than the slower, chronic, type C pain.

Typically, type C fibers are relatively heavily myelinated, large diameter fibers ("large fibers"), and type A fibers are relatively lightly myelinated, small diameter fibers ("small fibers"). Generally, the large fibers and the small fibers meet at the dorsal horn of the spinal cord, where a number of cell layers are located, including the substantia gelatinosa and several transmission cell layers.

The gate control theory suggests that some of the meeting points between the respective fibers and the cell layers are inhibitory, while others are excitory. Specifically, all large fiber meeting points are excitory. On the other hand, the small fiber meeting points in the substantia gelatinosa cell layer are inhibitory, while the small fiber meeting points in the transmission cell layers are excitory. The substantia gelatinosa cells also meet with the transmission cells of the respective large and small fiber junctures. These meeting points can become inhibitory for all information reaching the substantia gelatinosa due to a "gating effect."

Gating effect involves the substantia gelatinosa's reaction to stimuli from the respective fiber types. Specifically, it is believed that large fiber impulses have an inhibiting effect (gating effect) on the substantia gelatinosa's ability to allow both large fiber and small fiber impulses to pass to the transmission layers. On the other hand, it is believed that small fiber impulses have the opposite effect. Therefore, when both large and small fiber impulses occur simultaneously, the substantia gelatinosa would receive both inhibition and excitation. The net effect of this simultaneous stimulation is believed to result in the substantia gelatinosa's gating effect being less active than when receiving only large fiber stimulation yet being more active than when receiving only small fiber stimulation. The gate control theory supposes that the relative amount of activity in the large and small fibers may determine the amount of gating at the substantia gelatinosa and, in turn, the degree of pain impulse received at the transmission cell layers. Accordingly, an increase in the proportion of large fiber activity may lessen transmission cell activity, thereby decreasing pain perception. Conversely, an increase in the proportion of small fiber activity may increase transmission cell activity, thereby increasing pain perception.

Therefore, while not wishing to limit the present invention by theory, it is contemplated that a subject's pain perception during invasive medical procedures can be minimized by vibrating the skin proximate the puncture site before the skin is punctured. The vibration may increase the proportion of large fiber activity, thereby utilizing the aforementioned gating effect to lessen transmission cell activity resulting in decreased pain perception.

Figure 1:
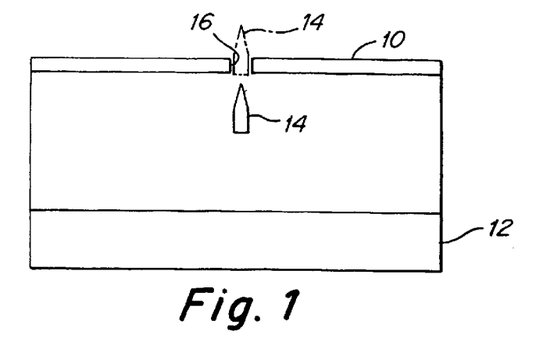
FIG. 1 is a schematic view of an aspect of the present invention.

With reference to FIG. 1, one embodiment of the apparatus of the present invention includes a receiving surface 10, a vibratory mechanism 12, and an invasive sharp 14. Receiving surface 10 is constructed to contact a portion of the subject's skin. Vibratory mechanism 12 is associated with receiving surface 10 such that vibratory mechanism 12 transmits vibrations through receiving surface 10 and to the subject's skin. Invasive sharp 14 is moveably disposed and permanently supported with respect to receiving surface 10. In operation, invasive sharp 14 reciprocates between a first position (shown in full line) in which it is spaced from receiving surface 10, away from the subject's skin, and a second position (shown in phantom line) in which at least a portion of invasive sharp 14 protrudes through an opening 16 in receiving surface 10.

Figure 2:
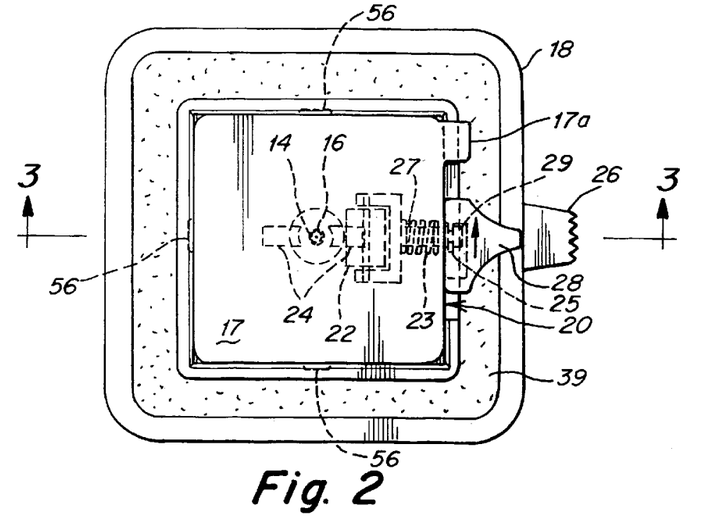
FIG. 2 is a top view of an apparatus according to one embodiment of the present invention.
Figure 3:
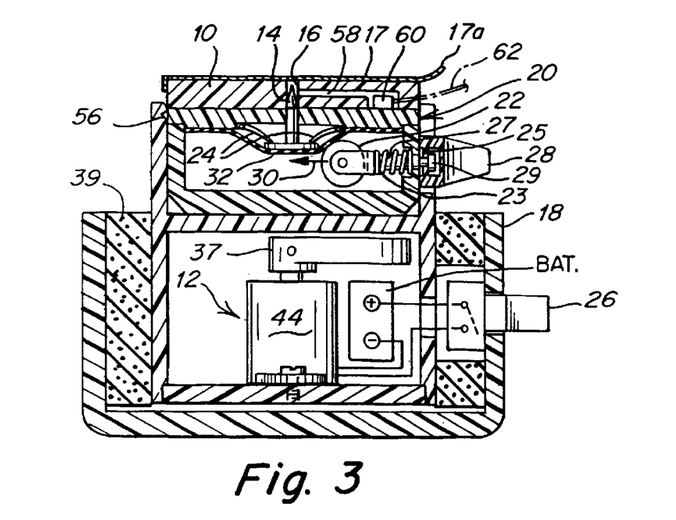
FIG. 3 is a cross-sectional schematic view taken along line 3—3 of FIG. 2.

As shown in FIGS. 2, 3, 4A, 4B, and 5 (where possible, like numbers are used to denote like elements), the apparatus of the present invention may optionally include a housing 18 and a removable module 20 disposed within the housing. As best seen in FIG. 3, module 20 may have a receiving surface 10 constructed to contact a portion of the subject's skin (not shown). An invasive sharp 14 may be moveably disposed within module 20 such that sharp 14 can reciprocate between a first position (shown in FIG. 4A), where sharp 14 lies below receiving surface 10, and a second position (shown in FIG. 4B), in which at least a portion of sharp 14 protrudes through an opening 16 in receiving surface 10 to puncture the subject's skin. A vibratory mechanism 12 (FIG. 3 and FIG. 5) associated with receiving surface 10 may be provided to transmit vibrations through the receiving surface and to the subject's skin. Optionally, a foil seal 17 may be adhesively attached to surface 10 to prevent contaminants from entering module 20 during transport and storage, and, if desired, a resealable foil seal may be used to prevent sample contamination after use. A tab 17a may be provided to facilitate removal of foil seal 17.

Figure 4A:
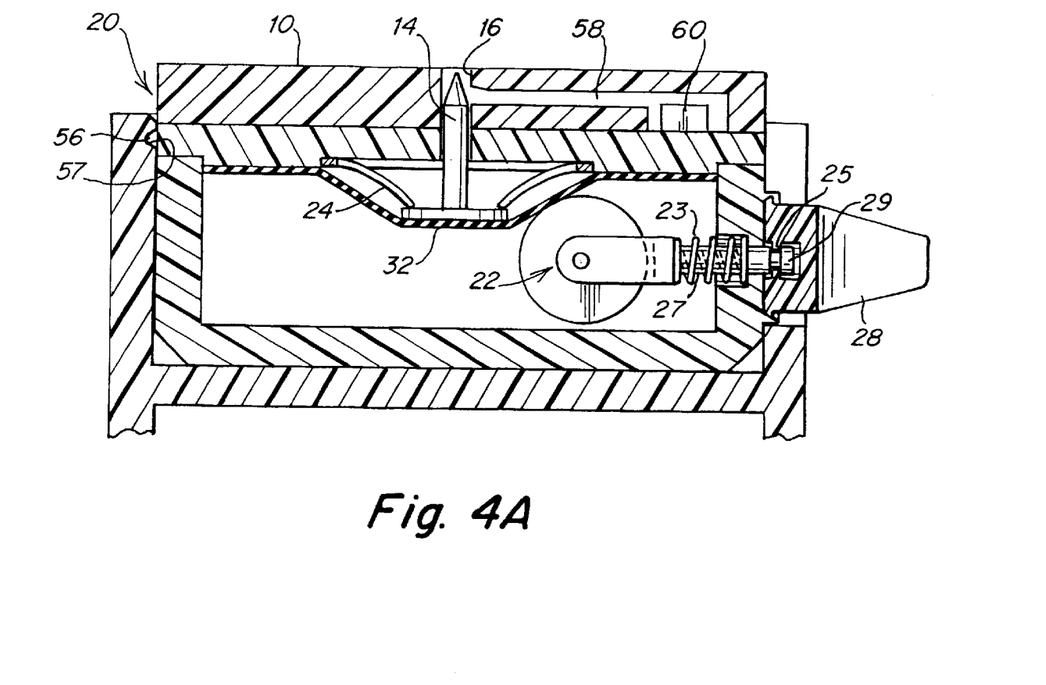
FIG. 4A is a cut-away, enlarged detail view of an aspect of the embodiment shown in FIG. 2.
Figure 4B:
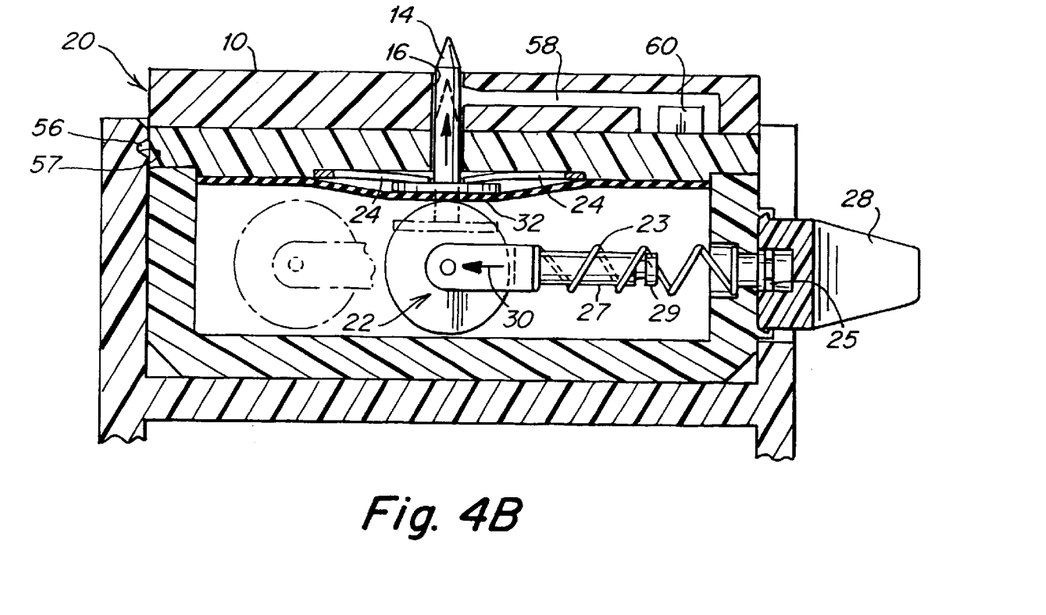
FIG. 4B is a cut-away, enlarged detail view of an aspect of the embodiment shown in FIG. 2.
Figure 6:
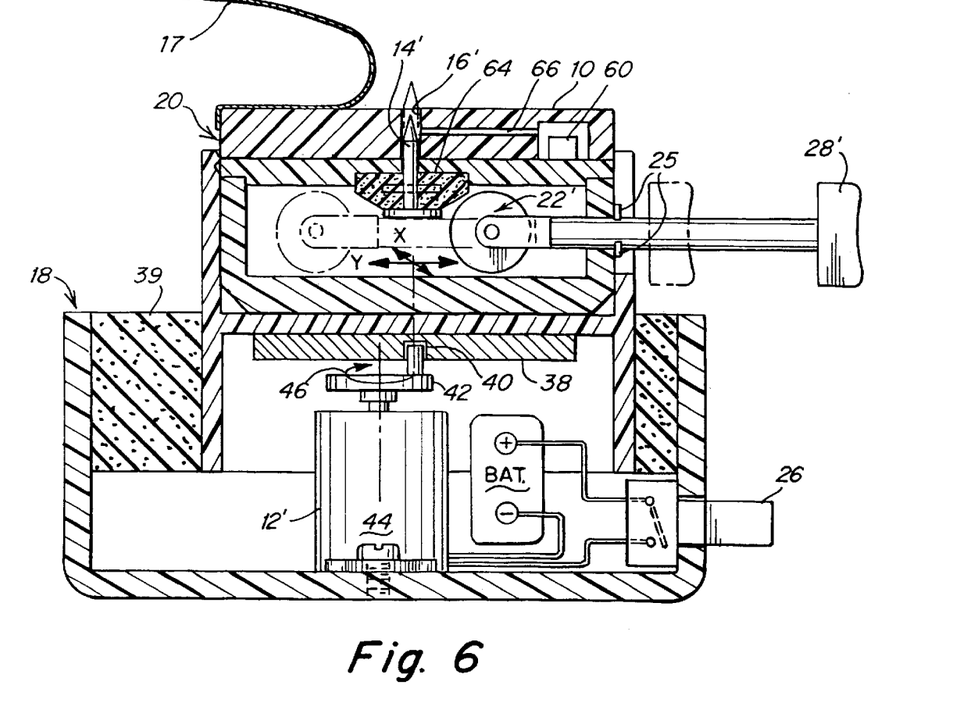
FIG. 6 is a cross-sectional schematic view of an aspect of an embodiment of the present invention.

The apparatus also includes an actuator to move sharp 14 from the first position to the second position. In one embodiment, such apparatus includes a roller unit 22 moveably disposed relative to invasive sharp 14 such that roller unit 22 can apply a force on sharp 14 to move it from the first position to the second position. It is contemplated that roller unit 22 can be spring loaded (FIGS. 2, 3, 4A, and 4B an) or, alternatively, manually operable (FIG. 6). In the spring-loaded embodiment, as shown in FIGS. 2, 3, 4A and 4B, roller unit 22 is restrained by handle 28 when sharp 14 is in its first position. In one embodiment, lips 25 on handle 28 extend beneath an enlarged head 29 disposed on the end of a plunger 27 to restrain handle 28. Movement of handle 28 in the direction of the arrow, as shown in FIG. 2, withdraws lips 25 from head 29 to release roller unit 22, allowing spring 23 to move unit 22 toward sharp 14 to urge sharp 14 from the first position to the second position, as shown in FIG. 4B. A resilient member may be associated with invasive sharp 14 to move the sharp from the second position to the first position when the force applied by roller unit 22 is removed. The resilient member may be a pair of leaf-type springs 24, as shown in FIGS. 3, 4A, and 4B or a resilient layer 64, as shown in FIG. 6. Of course, other known mechanisms may serve as the resilient member provided such articles render sufficient countering force to return invasive sharp 14 to the first position when the force applied by roller unit 22 is removed. In certain applications, the resilient member may have to provide enough force to withdraw invasive sharp 14 from the percutaneous tissue and the epidermal layer of the skin.

Figure 7:
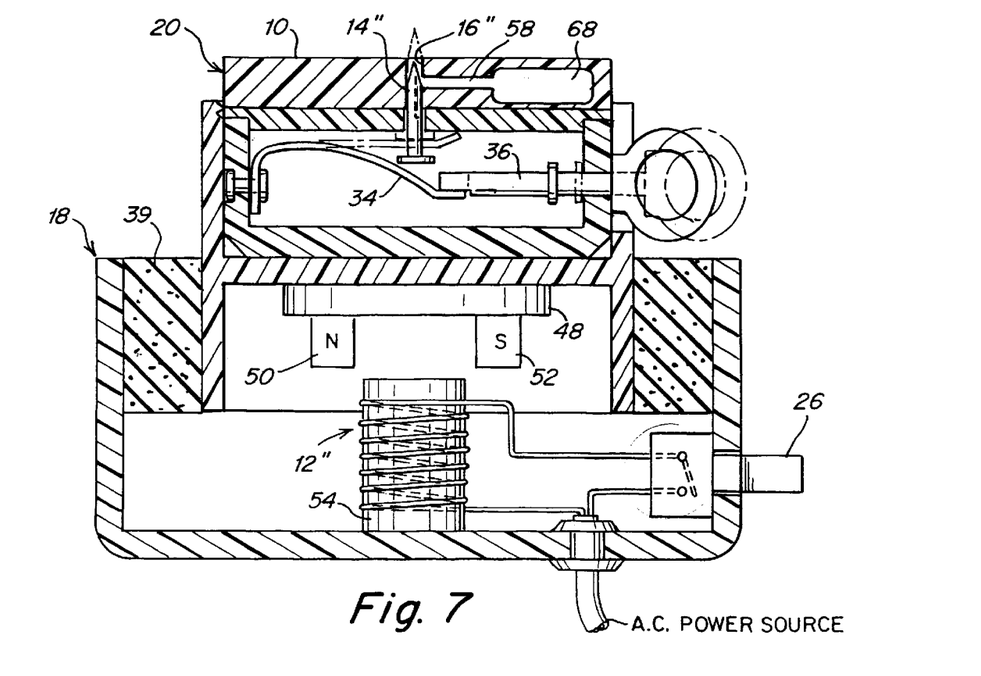
FIG. 7 is a cross-sectional schematic view of an aspect of an embodiment of the present invention.

In an alternative embodiment shown in FIG. 7, invasive sharp 14" is moved between the first position and the second position by a spring-like member 34, which is placed in a loaded position with a restraining member 36 or the like prior to placing the subject's skin on receiving surface 10. After sufficient vibration takes place, restraining member 36 is moved to allow spring-like member 34 to launch invasive sharp 14" into the subject's skin in a whip-like manner. Invasive sharp 14" can be provided with a channel 15 to allow flow through the sharp and into a reservoir 68 for sample collection or the like.

Invasive sharp 14 may be chosen from any instrument suitable for piercing a subject's skin during an invasive procedure. A non-exclusive list of invasive sharps include needles, lancets, scalpels, and the like. Invasive sharp may be hollow or solid and can be chosen by a skilled practitioner based on a given application.

In certain applications, it may be beneficial to repeatedly control the depth of the puncture made by the invasive sharp from subject to subject. For example, the distance from skin surface to bone in the thickest portion of the last segment of each finger of a newborn infant typically varies from 1.2 to 2.2 mm. Therefore, infant blood samples are typically collected through the plantar surface of the heel of the foot. However, in premature infants, the heel bone (calcaneus) may be no more than 2.4 mm beneath the plantar heel skin surface; thus, puncturing deeper than 2.4 mm on the plantar surface of the heel of small infants may risk bone damage. The unique configuration of the present invention allows puncture depth to be precisely controlled. Puncture depth may be controlled by sizing invasive sharp 14 according to the distance traveled between the first and second positions and/or by selecting and controlling the cross-sectional thickness of the resilient member and receiving surface 10. In this manner, the error involved in manually piercing an infant's heel can be dramatically reduced.

Vibratory mechanism 12 preferably transmits vibrations in the range of between about 5 Hz and about 150 Hz, and more preferably in the range of between about 30 Hz and about 40 Hz. Depending on various factors, including frequency, vibration of the subject's skin should continue from about 10 seconds to about 20 seconds before roller unit 22 is actuated. It will be appreciated by the skilled practitioner that vibration frequency and duration should be selected to sufficiently increase large fiber activity, thereby reducing the subject's pain perception proximate the contact point.

Figure 5:
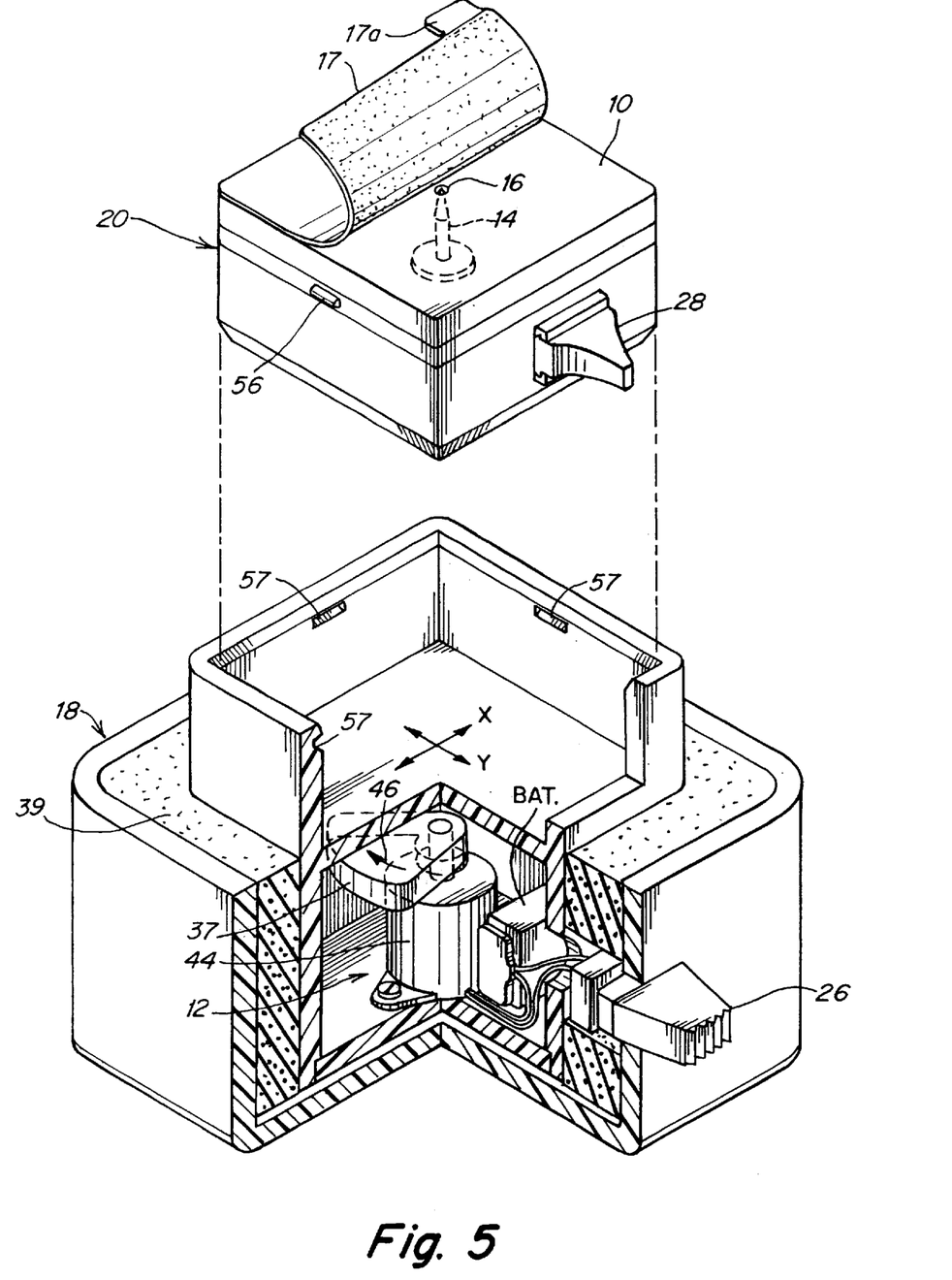
FIG. 5 is an exploded perspective view of an aspect of an embodiment of the present invention.

As shown in FIG. 3 and FIG. 5, one possible configuration for vibratory mechanism 12 includes an off-center, weighted cam 37 in association with a motor 44 such that the motor can rotate the eccentric cam in the direction of arrow 46. In operation, motor 44 rotates cam 37 which vibrates module 20 (and receiving surface 10) along the X-Y axes (denoted by arrows X and Y). Housing 18 may be provided with dampening foam 39 or the like to concentrate vibration in module 20 while minimizing movement of the entire apparatus on a support surface.

As shown in FIG. 6, an alternative configuration for vibratory mechanism 12' includes a vibrational plate 38 mounted for motion along the X-Y axes and having a circular slot 40 formed therein. A motor 44 rotates an eccentrically disposed cam 42 in the direction of arrow 46 within a circular slot 40. In operation, motor 44 rotates eccentric cam 42, which in turn reciprocates vibrational plate 38, resulting in vibratory motion of the plate along the X-Y axes.

As shown in FIG. 7, another possible configuration for vibratory mechanism 12" includes a vibrational plate 48 having a pair of permanent magnets 50, 52 disposed thereon and spaced apart from one another. An electromagnet 54 is placed proximate permanent magnets 50, 52. Electromagnet 54 may be chosen from art-recognized electromagnetic devices such as, for example, a metallic core surrounded by a conductive coil. When alternating current (e.g., from an external power source) is passed through such an electromagnet, its poles alternate, thereby causing electromagnet 54 to alternatingly attract and repel each permanent magnet 50, 52. This action displaces vibrational plate 48, resulting in vibratory motion of the plate.

Figure 8:
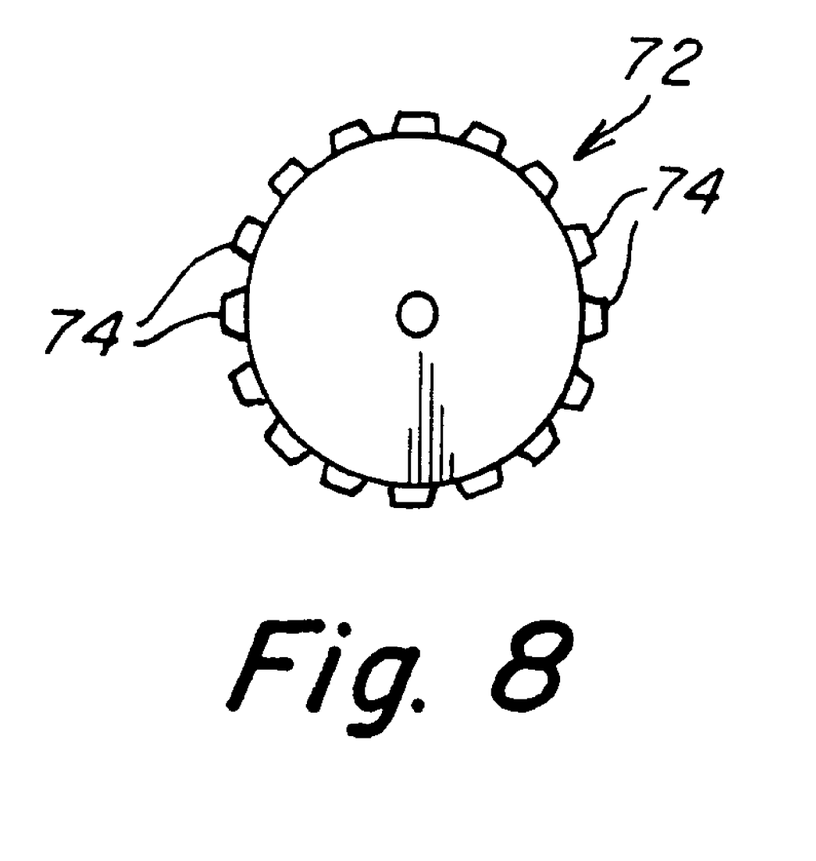
FIG. 8 is a side elevation view of an alternative embodiment of the roller of FIGS. 2–4B.

Optionally, roller unit 22 may include a roller having a roughened perimeter surface so that movement of the roughened roller transmits vibrations through the apparatus and to the receiving surface. An exemplary roughened roller 72 with bumps 74 is illustrated in FIG. 8. Depending on the length of the travel path of the roughened roller and the frequency of vibration resulting from its movement, it is contemplated that the roughened roller may be used instead of a vibratory unit or, alternatively, in concert with a vibratory unit to increase the intensity of the vibration immediately prior to the invasive procedure.

Optionally, the subject's skin may be warmed prior to piercing. Warming the puncture site can significantly increase arterial blood flow proximate the site, which may be important when specimens for pH and blood gas analysis are collected. One way of warming the puncture site is to provide a heating coil (not shown) in housing 18 and to select a highly thermally conductive material for the construction of receiving surface 10, such that heat passes by conduction to the receiving surface and, in turn, to the puncture site of the subject's skin. If employed, warming should take place at a temperature of no higher than about 42° C. to prevent both burning of the skin and significant chemical changes in the blood sample as it passes through the module.

As shown in FIGS. 2, 3, 4A, 4B, and 5, the apparatus may be modular, such that removable module 20, which may contain all invasive sharps and blood collection equipment, is held in place in housing 18 by mounting clips 56 or the like in connection with recesses 57. The mounting mechanism for module 20 should be sturdy enough to resist substantial movement while roller unit 22 is in motion, yet allow for easy removal and replacement of module 20. The modularity of this embodiment of the present invention greatly reduces health concerns for subsequent users, as well as the possibility of sample contamination.

Module 20 may be provided with a channel 58, which allows body fluid to flow by capillary action therethrough and directs the fluid to a point of use. The fluid may be directed to a sensor 60, which allows data to be quickly collected and transmitted in electronic form through a conductive cable 62 (shown in phantom in FIG. 3), or the like, to an integrated and/or remote system. It is also contemplated that channel 58 may direct a fluid sample to a self-contained storage area or reservoir 68 (FIG. 7) within module 20 so that the module can be removed and, if desired, transported to another location for subsequent sample analysis. To prevent significant changes in pH and blood gas values for extended periods, module 20 may be cooled during transportation.

In operation, a subject places a portion of his body on receiving surface 10. A switch 26 actuates vibratory mechanism 12, which transmits vibrations through surface 10 and to the subject's skin at a frequency and for a period of time sufficient to increase large fiber activity proximate the contact point, which as discussed above, reduces the amount of transmission cell activity and, in turn, reduces the subject's pain perception proximate the contact point. Roller unit 22 can then be actuated through a handle 28 or the like, which allows roller unit 22 to move (e.g., under pressure from a spring 23) in the direction of arrow 30 toward a support member 32. As seen in FIG. 4A, when roller unit 22 reaches a position beneath invasive sharp 14, the roller unit exerts a force through support member 32 and against invasive sharp 14 that drives it through opening 16 and into the subject's skin. As seen in FIG. 4B, roller unit 22 continues to move in the direction of arrow 30 until it no longer contacts support member 32. At this point, all forces exerted by roller unit 22 against invasive sharp 14 are removed, and the opposing force of leaf springs 24 withdraws invasive sharp 14 from the subject's skin and back into module 20. Optionally, the apparatus may be provided with a restraining member (not shown) to prevent sudden movement during the procedure.

As shown in FIG. 6, an alternative embodiment of the present invention includes receiving surface 10, invasive sharp 14, support member 32, and a manually operable roller unit 22'. However, instead of leaf springs, the resilient member of this embodiment may comprise a layer of resilient material 64, such as an elastomeric material or the like, which provides opposing force as roller unit 22' contacts support member 32 and which withdraws invasive sharp 14 from the subject's skin after roller unit 22' has moved beyond support member 32. In this embodiment, the body fluid may be directed by capillary action through a capillary tube 66 (such as a heparinized capillary tube) and to a point of use, such as sensor 60 or a storage area as discussed above. Use of a heparinized capillary tube lessens the possibility of the blood collecting air bubbles as it passes therethrough, which can be important if the sample is collected for pH and/or blood gas determinations. After the procedure, the capillary tube may be sealed with sealing clay or the like, or resealable foil seal 17 may be utilized to prevent significant air contamination.

It will be understood that each of the elements described herein, or two or more together, may also find utility in other applications differing from those described above. For example, other conventional medical methods may be used in conjunction with the present invention as dictated by specific requirements. Also, it is contemplated that the present invention, as described herein, can be used as part of a larger medical diagnostic or other system. While the invention has been illustrated and described as embodied in an apparatus and method for minimizing pain perception, it is not intended to be limited to the details shown, since various modifications and substitutions may be made without departing in any way from the spirit of the present invention as defined by the following claims.

What is claimed is:

1. An apparatus for reducing a subject's pain perception during a medical procedure, said apparatus comprising:
    a receiving surface constructed to contact a portion of the subject's skin, said receiving surface having an opening therethrough;
    a vibratory mechanism associated with the receiving surface such that the vibratory mechanism transmits vibrations through the receiving surface and to the subject's skin, to reduce pain perception, said vibratory mechanism transmitting vibrations having a frequency between about 5 Hz and about 150 Hz; and
    an invasive sharp supported with respect to said receiving surface and moveably disposed with respect to said receiving surface, said invasive sharp reciprocating between a first position in which the invasive sharp is spaced from the receiving surface, away from the subject's skin, and a second position in which at least a portion of the invasive sharp protrudes through the opening in the receiving surface.

2. The apparatus of claim 1, wherein the vibratory mechanism transmits vibrations having a frequency between about 30 Hz and about 40 Hz.

3. The apparatus of claim 1, further comprising a roller unit moveably disposed relative the invasive sharp such that the roller unit applies a force on the invasive sharp that moves the invasive sharp from the first position to the second position.

4. The apparatus of claim 3, further comprising a resilient member associated with the invasive sharp such that the resilient member moves the invasive sharp from the second position to the first position when the force applied by the roller unit is removed.

5. The apparatus of claim 4, wherein the resilient member is a spring.

6. The apparatus of claim 4, where in the resilient member is an elastomeric sheet.

7. The apparatus of claim 4 wherein said roller unit comprises:
    a support arm; and
    a rotatable roller mounted on said support arm, said roller being moveable from a first location spaced from the invasive sharp to a second location engaging the sharp, said roller moving in a direction generally perpendicular to a direction of movement of the invasive sharp from the first position to the second position.

8. The apparatus of claim 1, wherein the vibratory mechanism includes a roughened roller unit moveably disposed relative to the receiving surface such that movement of the roller unit transmits vibrations through the receiving surface.

9. A modular system for obtaining a blood sample from a subject with reduced pain perception, said system comprising:
    a housing;
    a removable module disposed within the housing, said module having a receiving surface constructed to contact a portion of the subject's skin, said receiving surface having an opening therethrough;
    an invasive sharp moveably disposed within the removable module such that the invasive sharp reciprocates between a first position in which the invasive sharp is withdrawn from the receiving surface within the module and a second position in which at least a portion of the invasive sharp protrudes through the opening in the receiving surface; and
    a vibratory mechanism associated with the receiving surface such that the vibratory mechanism transmits vibrations through the receiving surface and to the subject's skin to reduce pain perception, the vibratory mechanism transmitting vibrations having a frequency between about 5 Hz and about 150 Hz.

10. The system of claim 9, wherein the removable module includes a channel adapted to receive a body fluid from the subject and to direct the body fluid to a point of use.

11. The system of claim 10, wherein the channel includes a capillary tube.

12. The system of claim 9, wherein the vibratory mechanism transmits vibrations having a frequency between about 30 Hz and about 40 Hz.

13. The system of claim 9, further comprising a roller unit moveably disposed within the housing such that the roller unit is capable of applying a force on the invasive sharp that moves the invasive sharp from the first position to the second position.

14. The system of claim 13, further comprising a resilient member associated with the invasive sharp such that the resilient member moves the invasive sharp from the second position to the first position when the force applied by the roller unit is removed.

15. The system of claim 9, wherein the vibratory mechanism includes a roughened roller unit moveably disposed within the housing such that movement of the roller unit transmits vibrations through the receiving surface.

16. A method of reducing a subject's pain perception during a medical procedure, said method comprising the steps of:
    a) supporting an invasive sharp with respect to a receiving surface, said receiving surface having an opening therethrough for passage of the invasive sharp;
    b) vibrating the receiving surface while contacting at least a portion of the receiving surface with a portion of the subject's skin to vibrate the subject's skin for a period of time sufficient to reduce the subject's pain perception proximate a contact point, said vibrating step comprising the step of vibrating the receiving surface at a frequency between about 5 Hz and about 150 Hz;
    c) piercing the subject's skin with the sharp while the skin is contacting the receiving surface; and
    d) withdrawing the sharp from the subject's skin.

17. The method of claim 16, wherein the subject's skin is vibrated from about ten seconds to about twenty seconds prior to the piercing step.

18. The method of claim 16, wherein the piercing step comprises the step of actuating a roller unit moveably disposed relative to the invasive sharp such that the roller unit applies a force on the invasive sharp that moves the invasive sharp from a first position to a second position in which the sharp pierces the subject's skin.

19. The method of claim 18, wherein the step of withdrawing the invasive sharp from the subject's skin comprises the step of releasing the force applied by the roller unit on the sharp to allow a resilient member associated with the invasive sharp to move the invasive sharp from the second position to the first position.

20. An apparatus for reducing a subject's pain perception during a medical procedure, said apparatus comprising:

a receiving surface constructed to contact a portion of the subject's skin, said receiving surface having an opening therethrough;

a vibratory mechanism associated with the receiving surface such that the vibratory mechanism transmits vibrations through the receiving surface and to the subject's skin to reduce pain perception, said vibratory mechanism including a roughened roller unit moveably disposed relative to the receiving surface such that movement of the roller unit transmits vibrations through the receiving surface; and an invasive sharp supported with respect to said receiving surface and moveably disposed with respect to said receiving surface, said invasive sharp reciprocating between a first position in which the invasive sharp is spaced from the receiving surface, away from the subject's skin, and a second position in which at least a portion of the invasive sharp protrudes through the opening in the receiving surface.

* * * * *